(12) United States Patent
Van Spall et al.

(10) Patent No.: US 11,832,625 B2
(45) Date of Patent: Dec. 5, 2023

(54) SLAUGHTER DEVICE, SLAUGHTER INSTALLATION AND METHOD THEREOF

(71) Applicant: Meyn Food Processing Technology B.V., Oostzaan (NL)

(72) Inventors: Joy David Mike Van Spall, Oostzaan (NL); Ramzi Souli, Oostzaan (NL); Allardus Klaas Peddemors, Oostzaan (NL); Simon Kooij, Oostzaan (NL)

(73) Assignee: Meyn Food Processing Technology B.V., Oostzaan (NL)

( * ) Notice: Subject to any disclaimer, the term of this patent is extended or adjusted under 35 U.S.C. 154(b) by 56 days.

(21) Appl. No.: 17/553,072

(22) Filed: Dec. 16, 2021

(65) Prior Publication Data

US 2022/0192209 A1 Jun. 23, 2022

(30) Foreign Application Priority Data

Dec. 18, 2020 (NL) ..................................... 2027164

(51) Int. Cl.
*A22C 21/00* (2006.01)

(52) U.S. Cl.
CPC ...... *A22C 21/0015* (2013.01); *A22C 21/0053* (2013.01)

(58) Field of Classification Search
CPC ........................ A22C 21/0015; A22C 21/0053

USPC .......................................................... 452/53
See application file for complete search history.

(56) References Cited

U.S. PATENT DOCUMENTS

| 3,724,032 | A | * | 4/1973 | Harben, Jr. | .............. | A22B 3/06 |
| | | | | | | 452/63 |
| 3,918,125 | A | * | 11/1975 | Strandine | ........... | A22C 21/0015 |
| | | | | | | 452/54 |
| 2013/0052923 | A1 | | 2/2013 | Cornelissen | | |

FOREIGN PATENT DOCUMENTS

| DE | 1804084 A1 | 10/1969 |
| DE | 245354 A1 | 5/1987 |
| EP | 3628166 A1 | 4/2020 |
| JP | 2926483 B2 | 7/1999 |

OTHER PUBLICATIONS

Search Report for NL Patent Application No. 2027164 dated Sep. 8, 2021 (3 pages).

* cited by examiner

*Primary Examiner* — Richard T Price, Jr.
(74) *Attorney, Agent, or Firm* — Dority & Manning, P.A.

(57) ABSTRACT

Slaughter devices for poultry and methods thereof, which may include a track having a first guide and a second guide to define a slit for guiding the neck of the poultry. A rotary knife arranged in the first guide for cutting a first vein. A cylinder arranged in the first guide upstream of the rotary knife, which rotates in a first rotational direction to allow twisting of the neck in a second rotational direction.

9 Claims, 2 Drawing Sheets

SLAUGHTER DEVICE, SLAUGHTER INSTALLATION AND METHOD THEREOF

PRIORITY STATEMENT

The present application claims priority under 35 U.S.C. § 119 to Dutch patent application No. 2027164, filed on Dec. 18, 2020.

FIELD OF THE INVENTION

The subject matter of the present disclosure relates generally to slaughter devices for poultry and their methods of operation.

BACKGROUND OF THE INVENTION

Certain slaughter devices are known in the art and may include a single rotary knife arranged to provide a cut in the throat to reach a vein and/or artery as the neck moves along the track.

One problem for such devices is providing a cut in a reliable way, as the neck tends to twist when it conveys along the track due to friction. A possible way of solving this problem is providing two rotary knives to cut through at both sides of the neck while avoiding cutting the oesophagus, trachea, and vertebra of the poultry, such as in EP3628166. However, these solutions result in complex constructions. One or more devices and methods for solving this problem and/or others would be useful.

BRIEF DESCRIPTION OF THE INVENTION

Aspects and advantages of the invention will be set forth in part in the following description, or may be obvious from the description, or may be learned through practice of the invention.

In one exemplary embodiment, a slaughter device is provided having a rotary knife arranged to rotate in a first rotational direction to allow twisting of the neck in a second rotational direction opposite to the first rotational direction such that the rotary knife cuts through a second vein and/or artery at a second side of the neck opposite to the first side, a trachea and an oesophagus while avoiding cutting a vertebra in the neck of the poultry. In this way, a simpler construction having only one rotary knife to cut through the vein and/or artery of both sides of the neck can be achieved. For this embodiment, the slaughter device does not include a further rotary knife at a further side opposite to the side of the rotary knife, the further rotary knife being arranged to cut the second artery and/or vein of the second side of the neck of the poultry.

In additional exemplary aspects, a cylinder may engage the bill and/or the head for forcing the bill against the transport direction to cause twisting of the neck in the first rotational direction to expose a first side of the neck to cut through the vein and/or artery of the first side. Further, the cylinder may also cooperate with the rotary knife to cause rotation of the neck in the second rotational direction opposite to the first rotational direction. Once the bill and/or the head does not engage the cylinder anymore and therefore, the cylinder does not force the bill against the transport direction as the neck is being guided along the track, the neck tends to untwist by rotating in the second rotational direction to reach its natural position. This movement is also helped by the friction caused by the rotary knife in the first rotational direction. Thus, the chance that the rotary knife reaches the second vein and/or artery of the second side of the neck opposite to the first side can be increased, providing a more reliable cut through the neck.

In another exemplary aspect, the present invention is in the field of slaughter devices for cutting the throat (veins, arteries, oesophagus and trachea while avoiding a vertebra of the neck) of poultry being conveyed in a transport direction hanging by their legs by means of a conveyor line, wherein the poultry includes a head, a bill and a neck. More specifically, for this exemplary embodiment, the present invention relates to slaughter devices that may include a track having a first guide and a second guide to define a slit being arranged for guiding the neck of the poultry therein from an upstream end to a downstream end of the track as the conveyor line conveys the poultry; and a rotary knife included in the first guide of the track for cutting through a first vein and/or artery at a first side of the neck, a trachea and oesophagus whilst avoiding cutting a vertebra in the neck of the poultry; and a cylinder arranged in the first guide and upstream relative to the rotary knife for forcing the bill against the transport direction to cause twisting of the neck in a first rotational direction as the neck conveys along the track to expose the first vein and/or artery of the suspended poultry to be cut through by the rotary knife.

In another exemplary embodiment, the track may include a section arranged downstream relative to the cylinder that follows the contour of the rotary knife. In this way, the path along the track in which the rotary knife is cutting through the neck of the poultry being guided is increased and, therefore, the chances to reach the vein and/or artery of the second side is also increased. The section can follow the contour downwardly, so gravity may help in the rotational movement of the neck in the second rotational direction.

In another exemplary embodiment, the cylinder is rotatable about the first rotational direction. The cylinder is rotatable through contact with the bill and/or head of the passing poultry. In this way, twisting of the neck towards the first rotational direction is done smoothly.

In another exemplary aspect, the invention relates to a slaughter installation including a slaughter device having the features already described and a conveyor line for conveying in a transport direction the poultry to be slaughtered by the slaughter device while hanging by their legs.

In another exemplary embodiment, the conveyor line is arranged to maintain the poultry essentially vertically suspended while the neck is conveyed along the track between the cylinder and the rotary knife.

In still another exemplary aspect, the invention relates to a method for slaughtering poultry having a neck, a head and a bill. This exemplary method can include.

conveying in a transport direction by means of a conveying line the poultry being hanged from the feet such that the neck is conveyed along a track from an upstream end to a downstream end of a killing device;

cutting through a first vein and/or artery of a first side of the neck by means of a rotary knife; and twisting the neck in a first rotational direction by forcing the bill against the transport direction by means of a cylinder as the neck is being guided along the track to expose the first side of the neck;

cutting through, by means of the rotary knife, a second vein and/or artery located at a second side of the neck opposite to the first side, a trachea and oesophagus whilst avoiding cutting a vertebra in the neck of the poultry by rotating the rotary knife in the first rotational direction to cause twisting of the neck in a second rotational direction opposite to the first rotational direction.

In another exemplary embodiment, the track can include a section arranged downstream relative to the cylinder that follows the contour of the rotary knife and in the method the neck is guided along the contour of the rotary knife to cut through the neck from the first vein and/or artery to the second vein and/or artery.

BRIEF DESCRIPTION OF THE DRAWINGS

The invention will hereinafter be further elucidated with reference to the drawing of an exemplary embodiment of an apparatus according to the invention that is not limiting as to the appended claims.

In the figures.

DETAILED DESCRIPTION OF THE INVENTION

Figure 1A:
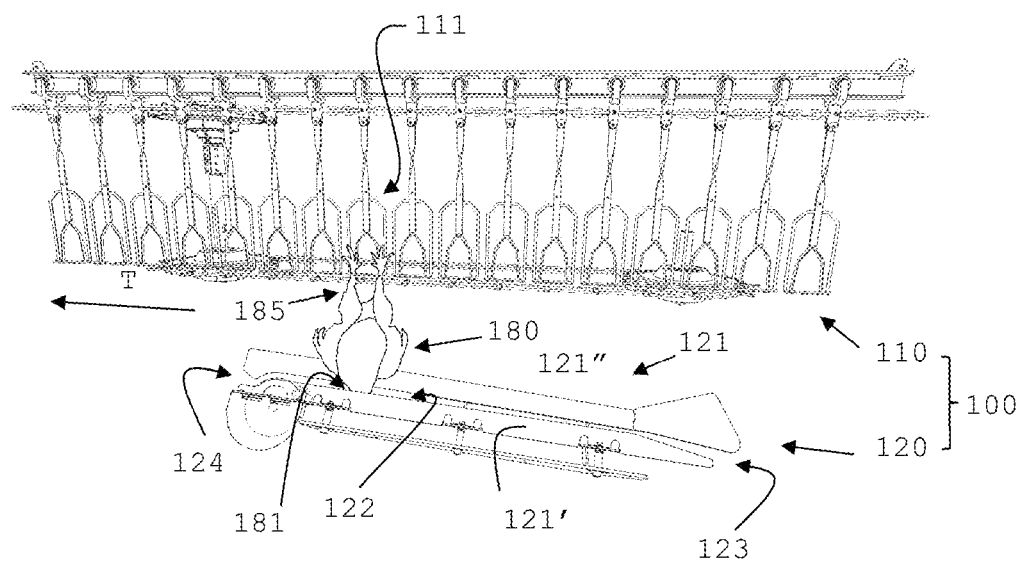
FIG. 1A shows a front view of a slaughter installation according to an exemplary embodiment the invention.
Figure 1B:
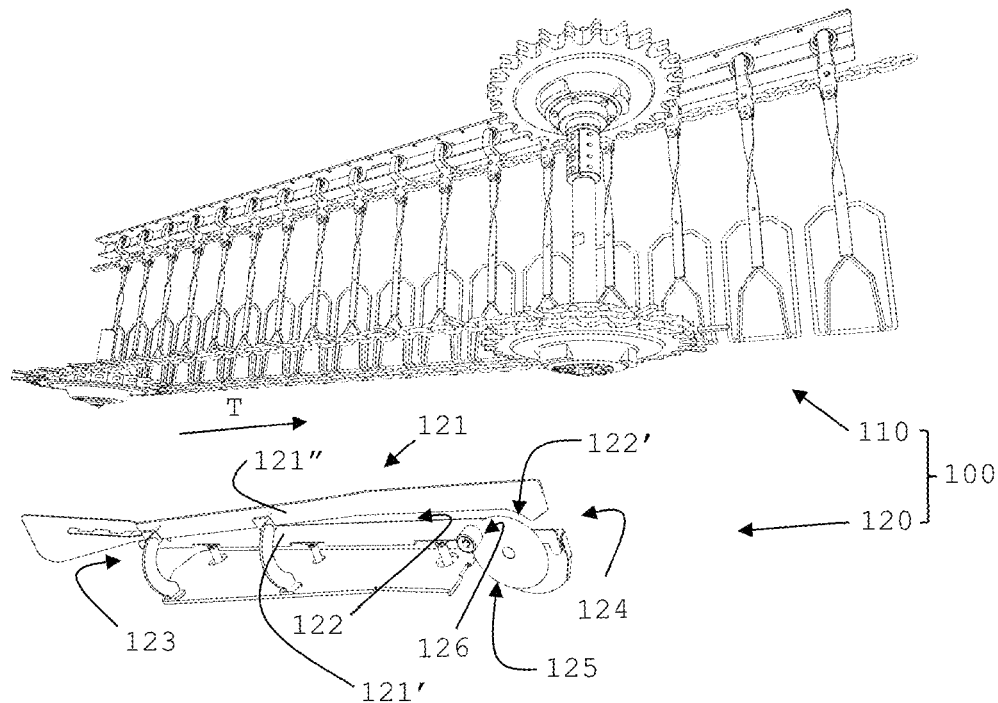
FIG. 1B shows an oblique rear view of the slaughter installation shown in FIG. 1A.

It is common knowledge that in general (live) poultry includes not only legs but also a neck, a head, and a bill. FIGS. 1A and 1B depict a slaughter installation 100 according to exemplary aspects of the invention. The exemplary slaughter installation 100 includes a conveyor line 110 with carriers 111 for suspending such poultry 180 by the legs 185 to convey the poultry 180 in a transport direction T.

The slaughter installation 100 also includes a slaughter device 120 having a guide track 121, wherein a neck 181 part of the poultry 180 moves along a slit 122 defined by a first guide 121' and a second guide 121" from an upstream end 123 to a downstream end 124 of the guide track 121.

FIG. 1B shows the exemplary slaughter installation 100 in an obliquely view from below, and from this figure it is apparent that the exemplary slaughtering device 120 includes at the first guide 121' a rotary knife 125 and a cylinder 126, the latter being upstream relative to the rotary knife 125. This view also shows how a section 122' of the slit is arranged to follow the contour of the rotary knife 125.

Figure 2A:
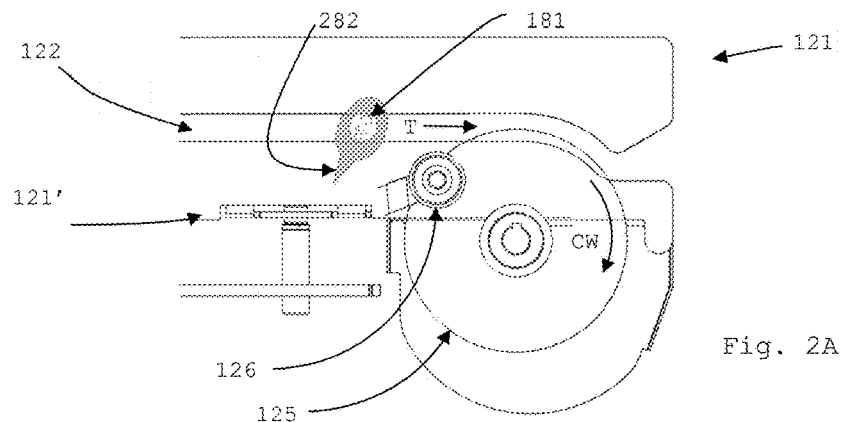
FIGS. 2A, 2B, 2C and 2D show different steps during the cutting process of the exemplary slaughter installation from an expansion of the rear view of FIG. 1B.
Figure 2B:
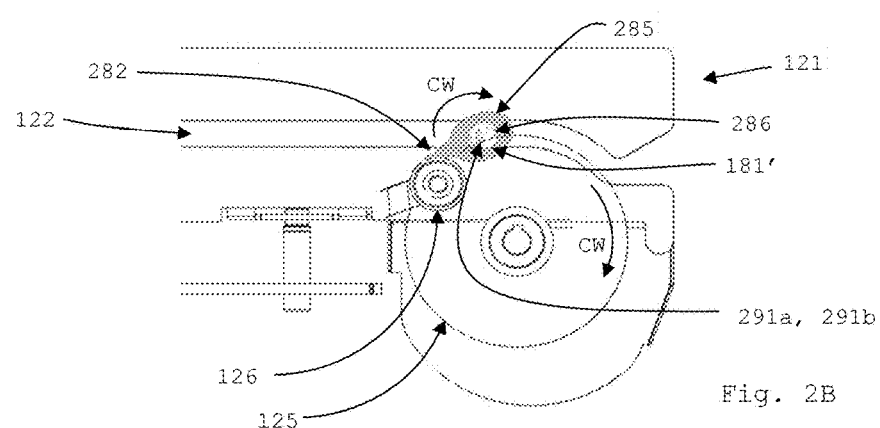

FIGS. 2A to 2B focus on the how the cylinder 126 and rotary knife 125 work together to slaughter poultry from the rear view as in FIG. 1B.

In a first exemplary step (FIG. 2A), the poultry is conveyed such that the neck 181 is guided along the slit 122 of the track 121 towards the cylinder 126, with a bill 282 pointing downwards. This step is known by the skilled person and, therefore, no further elucidation is required. It might happen that the neck 181 may twist causing that the bill 282 is not exactly pointing downwards due to friction caused by the track on the neck 181 as the poultry is conveyed.

In a second exemplary step (FIG. 2B), the neck of the poultry reaches a point along the slit 122 in which the bill 282 or the head 285 engages the cylinder 126. In the present embodiment, the latter is rotatable through contact. From this moment, as the neck is further conveyed along the slit 122, the cylinder 126, by engaging the head 285 and the bill 282 forces the bill 282 against the transport direction and the neck 181 will twist in a first rotational direction represented by arrow CW such that the bill 282 is pointing substantially against the transport direction T. In this view, the first rotational direction is clockwise about an axis (not shown) transverse to the transport direction T of the suspended poultry 180. The twisting motion of the head 285 of the poultry 180 leads to the shown orientation of the bill 282 to expose a first side 181' of the neck 181, which enables that the rotary knife 125 can cut through a first artery 291a and vein 291b without cutting a vertebra 286.

Figure 2C:
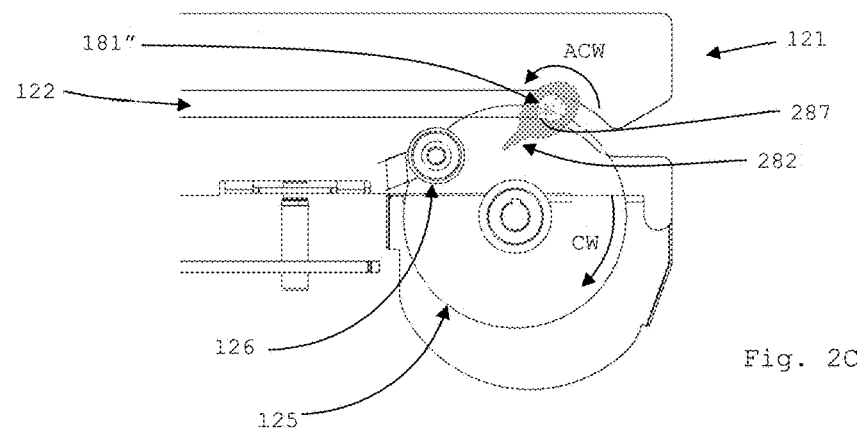
Figure 2D:
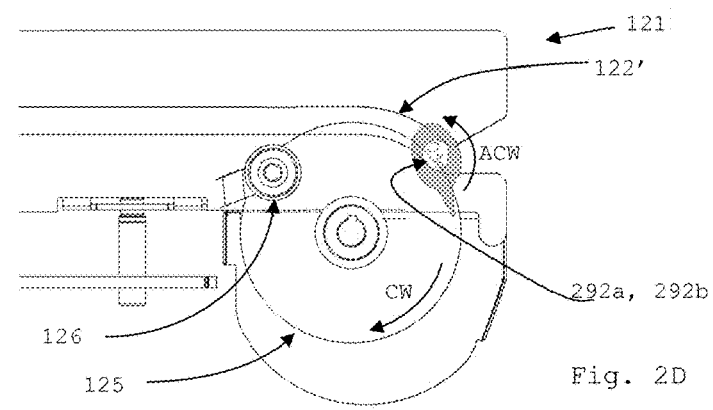

Once the first artery 291a and vein 291b are cut, the neck keeps on being conveyed along the slit 122 of the track 121 and the bill 282 disengages the cylinder 126 (see FIG. 2C). At this moment, due to the twisting caused by the cylinder 126, the neck tends to untwist following a second rotational direction as represented by arrow ACW such that the bill points again downwards. In this view, the second rotational direction is anti-clockwise. Since the rotary knife 125 is arranged to cut by rotating in the first rotational direction CW, it will contribute to keep on twisting the neck of the poultry 180 in the second rotational direction ACW towards a second side 181" of the neck 181 cutting through oesophagus 287 and trachea (not depicted for the sake of clarity in the drawing).

Finally, the neck is guided along a last section 122' that follows the contour of the rotary knife 125. This in combination with the twisting of the neck in the second rotational direction ACW caused by the rotary knife 125 will allow the rotary knife 125 to cut through a second vein 292a and artery 292b of the second side 181".

Although the invention has been discussed in the foregoing with reference to an exemplary embodiment of the slaughter device of the invention, the invention is not restricted to this particular embodiment which can be varied in many ways without departing from the invention. It is for instance possible to change the convey the poultry such that the bill 282 is pointing upwards when the neck is conveyed along the track 121, and the cylinder 126 and rotary knife 125 are arranged above relative to the slit 122.

The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

The invention claimed is:

1. A slaughter device for poultry being conveyed in a transport direction hanging by their legs using a conveyor line, wherein the poultry includes a head, a bill, and a neck, the slaughter device comprising:
    a track having a first guide and a second guide to define a slit for guiding the neck of the poultry therein from an upstream end to a downstream end of the track as the conveyor line conveys the poultry;
    a rotary knife arranged in the first guide of the track for cutting through a first vein, first artery, or both, at a first side of the neck; and
    a cylinder arranged in the first guide and upstream relative to the rotary knife for forcing the bill against the transport direction to cause twisting of the neck in a first rotational direction as the neck conveys along the track to expose the first vein, the first artery, or both of the suspended poultry to be cut through by the rotary knife;

wherein the rotary knife is arranged to rotate in the first rotational direction to allow twisting of the neck in a second rotational direction opposite to the first rotational direction such that the rotary knife cuts through a second vein, second artery, or both, at a second side of the neck opposite to the first side, a trachea and an oesophagus while avoiding cutting a vertebra in the neck of the poultry.

2. The slaughter device according to claim 1, wherein the slit of the track includes a section arranged downstream relative to the cylinder that follows the contour of the rotary knife.

3. The slaughter device according to claim 1, wherein the cylinder is rotatable about the first rotational direction.

4. The slaughter device according to claim 3, wherein the cylinder is rotatable through contact with the bill and or head of the passing poultry.

5. The slaughter device according to claim 1, wherein the slaughter device does not include a further rotary knife at the second guide of the track, the further rotary knife arranged to cut the second artery, second vein, or both of the second side of the neck of the poultry.

6. A slaughter installation including a slaughter device according to claim 1 and a conveyor line for conveying in a transport direction and while hanging by their legs the poultry to be slaughtered by the slaughter device.

7. The slaughter installation according to claim 6 wherein the conveyor line is arranged to maintain the poultry essentially vertically suspended while the neck is conveyed along the track between the cylinder and the rotary knife.

8. A method to slaughter poultry that includes a neck, a head, and a bill, the method comprising:
    using a conveying line to convey the poultry being hanged from the feet in a transport direction such that the neck is conveyed along a track from an upstream end to a downstream end of a killing device; and
    cutting through a first vein, a first artery, or both of a first side of the neck;
    twisting the neck in a first rotational direction about an axis transverse to the transport direction by forcing the bill against the transport direction by means of a cylinder being arranged upstream relative to the rotary knife as the neck is being guided along the track to expose the first side of the neck; and
    using a rotary knife to cut through from the first vein, the first artery, or both to a second vein, second artery, or both, located at a second side of the neck opposite to the first side, a trachea and oesophagus whilst avoiding cutting a vertebra in the neck of the poultry by rotating the rotary knife in the first rotational direction to cause twisting of the neck in a second rotational direction opposite to the first rotational direction.

9. The method according to claim 8, wherein the track comprises a section arranged downstream relative to the cylinder that follows the contour of the rotary knife, and the method further comprising guiding the neck along the contour of the rotary knife to cut through the neck from the first vein, first artery, or both to the second vein, second artery, or both.

* * * * *